United States Patent [19]

Ikenaga et al.

[11] Patent Number: 4,962,550
[45] Date of Patent: Oct. 16, 1990

[54] TOILET WITH URINE CONSTITUENT MEASURING DEVICE

[75] Inventors: Takao Ikenaga; Toshifumi Shigematsu, both of Kanagawa; Masatoshi Yada, Fukuoka; Shigeru Makita; Hitoshi Kitaura, both of Kyoto, all of Japan

[73] Assignees: Toto, Ltd., Fukuoka; Omron Tateisi Electronics Co., Kyoto, both of Japan

[21] Appl. No.: 235,504

[22] Filed: Aug. 24, 1988

[30] Foreign Application Priority Data

| Aug. 24, 1987 | [JP] | Japan | 62-209966 |
| Aug. 24, 1987 | [JP] | Japan | 62-209967 |
| Aug. 24, 1987 | [JP] | Japan | 62-209968 |
| Aug. 24, 1987 | [JP] | Japan | 62-209969 |
| Aug. 24, 1987 | [JP] | Japan | 62-209970 |
| Aug. 24, 1987 | [JP] | Japan | 62-209971 |
| Aug. 24, 1987 | [JP] | Japan | 62-209972 |
| Aug. 24, 1987 | [JP] | Japan | 62-128246 |
| Aug. 24, 1987 | [JP] | Japan | 62-128247 |

[51] Int. Cl.⁵ ............... E03D 11/00; A61B 5/00
[52] U.S. Cl. .................... 4/420; 4/314; 4/661; 128/760
[58] Field of Search ............ 4/314, 420, 661; 128/760, 771

[56] References Cited

U.S. PATENT DOCUMENTS

| 4,466,445 | 8/1984 | Abrams | 128/736 |
| 4,524,777 | 6/1985 | Kisioka et al. | 128/677 |
| 4,554,687 | 11/1985 | Carter et al. | 4/144.2 |
| 4,636,474 | 1/1987 | Ogura et al. | 4/661 X |
| 4,860,767 | 8/1989 | Maekawa | 128/760 |
| 4,901,736 | 2/1990 | Huang | 128/760 |

FOREIGN PATENT DOCUMENTS

| 57-59168 | 4/1982 | Japan . | |
| 57-183969 | 5/1983 | Japan . | |
| 59-217844 | 2/1984 | Japan . | |
| 60-233551 | 5/1984 | Japan . | |
| 60-117157 | 6/1985 | Japan . | |
| 60-155977 | 8/1985 | Japan . | |
| 3021555 | 1/1988 | Japan | 4/314 |
| 987517 | 3/1965 | United Kingdom | 4/420 |

Primary Examiner—Charles E. Phillips
Attorney, Agent, or Firm—Lowe, Price, Leblanc, Becker & Shur

[57] ABSTRACT

A toilet has a device for measuring constituents of voided urine. The toilet has a urine reservoir having a surface contiguous to a bowl surface including a urine receiving surface. Urine examined by the measuring device is sampled from the urine reservoir.

25 Claims, 6 Drawing Sheets

| MORNING HEALTH DATA | | | |
|---|---|---|---|
| URINE EXAMINATION | GLUCOSE | 0 | mg/dl |
| | ALBUMIN | 0 | mg/dl |
| | UROBILIN | 0.5 | mg/dl |
| | OCCULT BLOOD | 0 | mg/dl |
| | TOTAL ANALYSIS | NORMAL/ BE CAREFUL | |
| BLOOD PRESSURE | HIGHEST | 128 | mmHg |
| | LOWEST | 78 | mmHg |
| PULSE RATE | | 63 | p/m |
| BODY TEMPERATURE | | 36.8 | °C |
| BODY WEIGHT | | 65.8 | kg |

FIG.15

TOILET WITH URINE CONSTITUENT MEASURING DEVICE

BACKGROUND OF THE INVENTION

1. Field of the Invention

The present invention relates to a toilet having a device for inspecting various constituents of urine voided by a user of the toilet.

2. Description of the Relevant Art

Some known toilets have an ability to extract and analyze voided urine to detect the amounts of constituents such as glucose of the urine for daily health care of users of the toilets, as disclosed Japanese Laid-Open Utility Model Publication No. 59-183969 and Japanese Laid-Open Patent Publication No. 60-233551.

The toilet disclosed in the former publication includes a tube for delivering sampled urine to an analyzer. Use of the tube for urine delivery is problematic in that the joints of the tube are prone to trouble and the tube is liable to get clogged.

According to the latter publication, a urine sensor is disposed in a small bowl for receiving voided urine, the small bowl being mounted on the distal end of an arm extending over the bowl of the toilet. Since the small bowl is positioned in the bowl of the toilet while urine is being voided, the user may find it awkward to use the toilet.

SUMMARY OF THE INVENTION

According to the present invention, a toilet comprises a bowl surface including a urine receiving surface, a urine reservoir having an upper surface contiguous to the bowl surface and the urine receiving surface, and a device for measuring constituents of urine sampled from the urine reservoir.

The toilet with the device for measuring constituents of urine is highly liable and less awkward to use.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figures 1, 2, 3, 4:
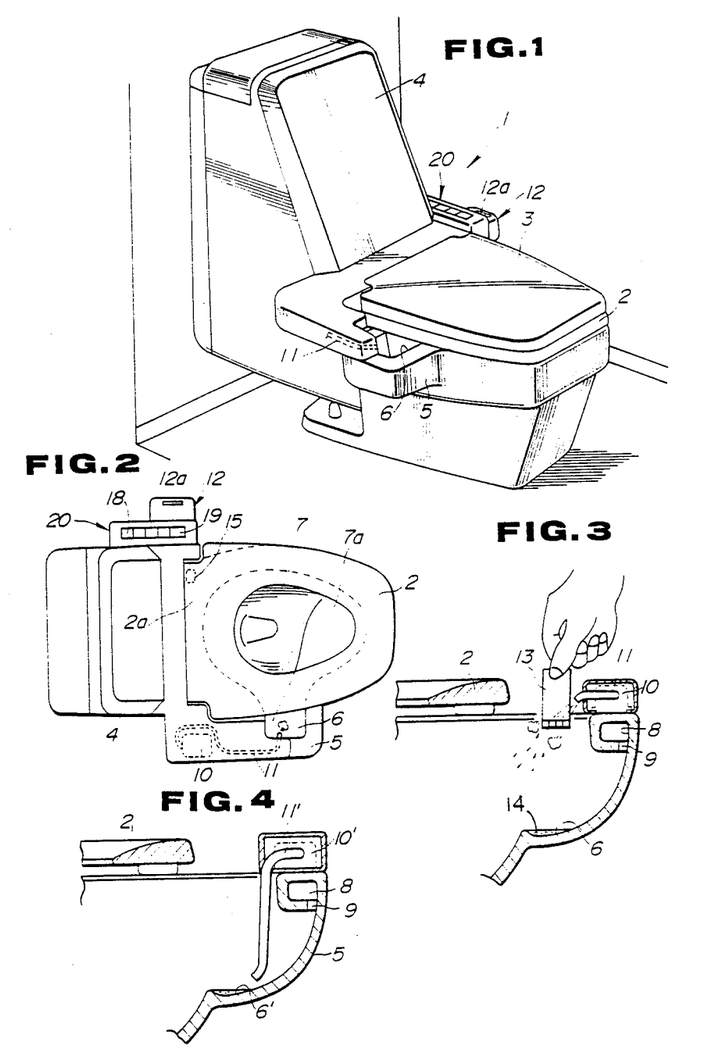
FIG. 1 is a perspective view of a toilet having a device for measuring constituents of voided urine according to a first embodiment of the present invention.
FIG. 2 is a plan view of the toilet shown in FIG. 1.
FIG. 3 is a fragmentary vertical cross-sectional view of a urine reservoir in the toilet.
FIG. 4 is a view similar to FIG. 3, showing a modification of a pipe extending from an air pump.

As shown in FIG. 1, a toilet 1 includes a seat 2 and a cover 3 which are openably and closably mounted on a front upper surface of the toilet 1, and a box 4 joined to the rear portion of the toilet 1 and housing a water tank therein.

The toilet 1 includes a laterally outwardly projecting portion 5 having a urine reservoir 6 therein. As illustrated in FIG. 2, the urine reservoir 6 has an upper surface contiguous to a bowl surface 7 of the toilet 1. The bowl surface 7 includes a portion 7a for receiving voided urine, the portion 7a being joined to the urine reservoir 6 by a surface which is gradually inclined downwardly from the portion 7 toward the urine reservoir 6 for allowing a portion of the voided urine to flow by gravity into the urine reservoir 6.

As shown in FIG. 3, the toilet 1 has an upper double-walled construction surrounding the bowl surface 7 and defining therein a flush water passage 8. Flush water supplied to the flush water passage 8 is discharged through holes 9 onto the bowl surface 7 and the urine reservoir 6.

An air pump 10 is mounted on a rear upper surface of the toilet 1, and a pipe 11 extending from the air pump 10 has a tip end disposed above the urine reservoir 6. A sensor 12 for detecting glucose, albumin, urobilin, occult blood, and the like in voided urine, and an operating unit 20 having a button 18 for operating the air pump and a series of buttons 19 for washing parts of the body of a user of the toilet 1 are attached to a side of the toilet 1 which is opposite to the urine reservoir 6.

For measuring various constituents of voided urine, as shown in FIG. 3, the user holds a piece of test paper 13, dips its lower end in a pool of urine 14 in the urine reservoir 6, lifts the test paper 13 out of the urine pool 14, then positions the test paper 13 in front of the tip end of the pipe 11, discharges air from the air pump 10 through the pipe 11 toward the test paper 13 to blow away excessive urine off the test paper 13, and inserts the test paper 13 into a slot 12a of the sensor 12 for urine examination.

A seat sensor 15 is mounted on a rear proximal end 2a of the toilet seat 2 for detecting when the user is seated on the seat 2. The seat sensor 15 is operatively coupled to an automatic water valve (not shown) for closing the same while the user is seated on the seat 2. Since the toilet 1 is not flushed with water while the data of the voided urine are being measured, the urine sampled for measurement is not drained or diluted by water through an oversight of the user. While the seat sensor 15 has been described as being operatively coupled to the automatic water valve, the automatic water valve may instead be operatively coupled to the urine sensor 12 so that the water valve can be opened after urine data have been measured.

FIG. 4 shows a modification of the pipe 11 extending from the air pump 10 in the above embodiment. As shown in FIG. 4, a pipe 11' from an air pipe 10' has a tip end extending near a urine reservoir 6'.

For measuring various constituents of urine, the air pump 10' is actuated before urine is voided to discharge air from the tip end of the pipe 11' to blow away water from the urine reservoir 6'. Then, urine is voided to retain a portion of the voided urine in the urine reservoir 6', and a piece of test paper is dipped in the urine pool in the urine reservoir 6'. The test paper is inserted into the urine sensor to analyze the constituents of the urine.

In the embodiment of FIG. 4, the air pump 10' is employed to remove water from the urine reservoir 6'. However, any remaining water in the urine reservoir 6' may be removed under suction by a suction device.

Figure 5:
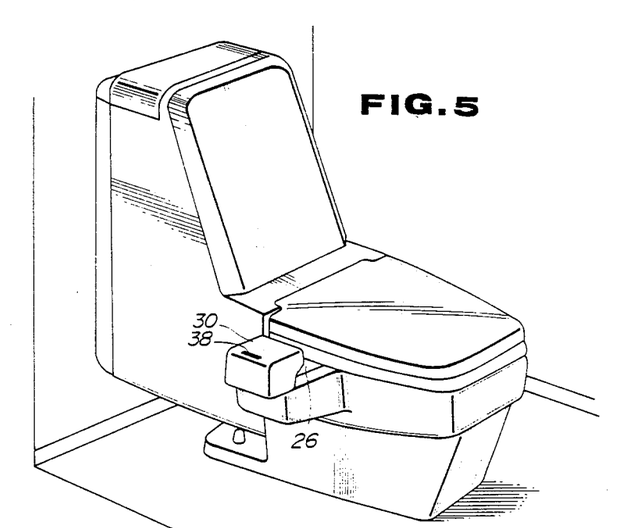
FIG. 5 is a perspective view of a toilet having a device for measuring constituents of voided urine according to a second embodiment of the present invention.
Figure 6:
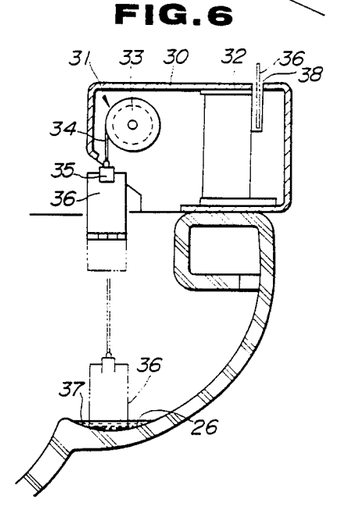
FIG. 6 is a fragmentary vertical cross-sectional view showing the relationship between a urine reservoir and a urine constituent measuring device in the toilet shown in FIG. 5.

FIGS. 5 and 6 show a toilet according to a second embodiment of the present invention. In this embodiment, a case 30 is disposed above a urine reservoir 26 and houses a lifting/lowering mechanism 31 and a sensor 32 therein. The lifting/lowering mechanism 31 comprises a drum 33 rotatable by a motor (not shown), a wire 34 wound around the drum 33, and a clip 35 attached to the tip end of the wire 34.

For detecting various constituents such as glucose, albumin, urobilin, and occult blood of urine, an unused piece of test paper 36 is attached to the clip 35 by the user, the motor is energized to rotate the drum 33 to lower the test paper 36 with the wire 34 to the urine reservoir 26 until the lower end of the test paper 36 is dipped in a pool of urine 37. Then, the drum 33 is rotated in the opposite direction to elevate the test paper 36 to which urine is applied, the test paper 36 is detached from the clip 35, and then the test paper 36 is inserted into a slot 38 of the sensor 32.

While the lifting/lowering mechanism 31 is shown as comprising the drum 33, the wire 34, and the clip 35, the lifting/lowering mechanism 31 may be of any of various other constructions.

Figure 7:
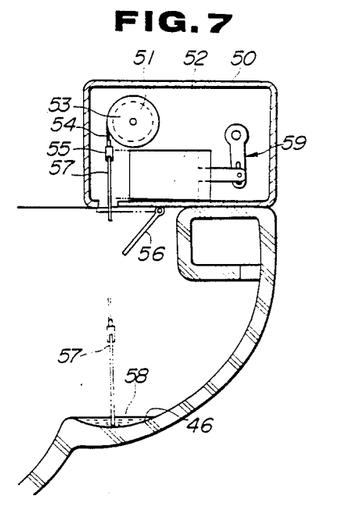
FIG. 7 is a view similar to FIG. 6, illustrating a toilet with a device for measuring constituents of voided urine according to a third embodiment of the present invention.

FIG. 7 illustrates a toilet according to a third embodiment of the present invention. In this embodiment, while a piece of test paper to which urine is applied is being attached to a clip of a lifting/lowering mechanism, the constituents of the urine are analyzed by a sensor.

More specifically, a case 50 is disposed above a urine reservoir 46, and a lifting/lowering mechanism 51 which is the same as that shown in FIG. 6 and a sensor 52 which is different from that shown in FIG. 6 are housed in the case 50. The sensor 52 is movable back and forth by a link mechanism 59, the sensor 52 comprising a photoelectric sensor of the reflecting photometry type. An openable and closable lid 56 is attached to the lower surface of the case 50. During a measuring process the lid 56 is closed to prevent extraneous light from entering the case 50 in which the urine is measured.

For measuring constituents of voided urine, an unused piece of test paper 57 is attached to the clip 55 by the user, and the motor is energized to rotate the drum 53 to lower the test paper 57 with the wire 54 toward the urine reservoir 46. At this time, the lid 56 is turned downwardly or opened out of physical interference with the test paper 57 being lowered. The lower end of the test paper 57 is dipped in a pool of urine 58, and then the drum 53 is rotated in the opposite direction to lift the test paper 57 to which urine is attached. The test paper 57, when it is lifted to its uppermost position, is accommodated within the case 50, whereupon the lid 56 is closed. Thereafter, the constituent data of the urine are measured by the sensor 52.

Figure 8:
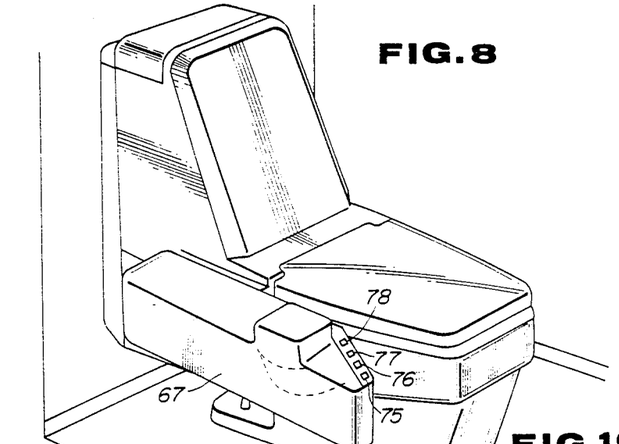
FIG. 8 is a perspective view of a toilet having a device for measuring constituents of voided urine according to a fourth embodiment of the present invention.
Figure 9:
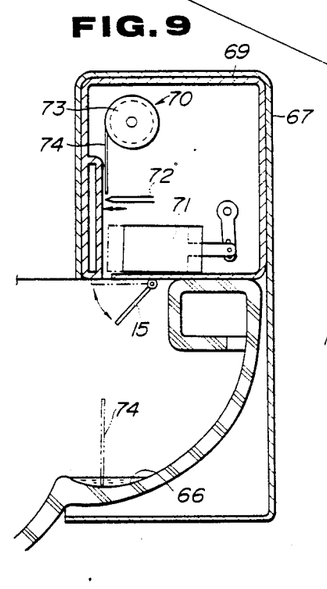
FIG. 9 is a view similar to FIG. 6, showing the toilet of FIG. 8.

FIGS. 8 and 9 show a toilet according to a fourth embodiment which is a modification of the arrangement illustrated in FIG. 7. According to the fourth embodiment, a case 69 disposed upwardly of a urine reservoir 66 houses a lifting/lowering mechanism 70, a sensor 71, and a cutter 72 serving as a device for discarding used test paper. The lifting/lowering mechanism 70 has a drum 73 rotatable by a nonillustrated motor and an elongate continuous sheet of test paper 74 wound around the drum 73. The sensor 71 is of the same type as shown in FIG. 7.

The urine reservoir 66 and the case 69 are covered with a cover 67 which has buttons 75, 76, 77, 78 for operating the lifting/lowering mechanism 70, the sensor 71, and the cutter 72 within the case 69.

For analyzing constituents of urine, after the user of the toilet voids urine, the user pushes the button 75 near the case 69 to energize the motor to unwind the test paper 74 from the drum 73 and lower the test paper 74 until the lower end thereof is dipped in a pool of urine in the urine reservoir 66. Then, the button 76 is pushed to reverse the motor to elevate the test paper 74, and the button 78 is depressed to activate the sensor 71 to analyze the urine applied to the lower end of the test paper 74. Thereafter, the button 78 is pushed to cause the cutter 72 to cut off the test paper 74 at a position above the urine-applied portion of the test paper 74. The cut piece then falls into the urine reservoir 66 and is thereafter discharged by water which flushes the toilet.

In the illustrated embodiment, the user is not required to touch the test paper when the urine is measured, and hence no urine will be applied to fingers of the user.

Figure 10:
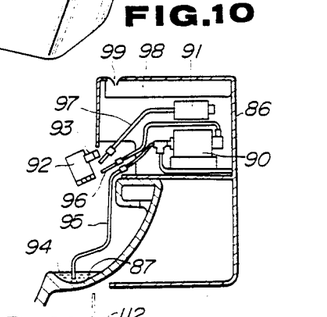
FIG. 10 is a view similar to FIG. 6, illustrating a toilet with a device for measuring constituents of voided urine according to a fifth embodiment of the present invention.
Figure 11:
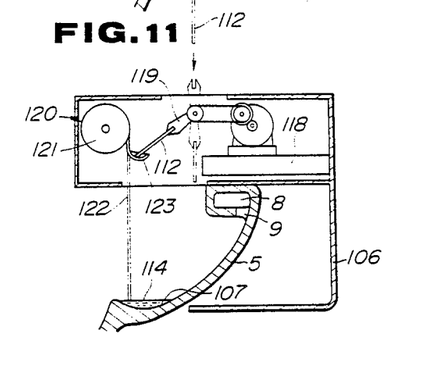
FIG. 11 is a view similar to FIG. 6, illustrating a toilet with a device for measuring constituents of voided urine according to a sixth embodiment of the present invention.

FIGS. 10 and 11 show fifth and sixth embodiments, respectively, of the present invention in which different devices are housed in covers that cover urine reservoirs.

In FIG. 10, a urine suction pump 90, an air pump 91, and a holder 93 for holding a piece of test paper 92 are disposed above a urine reservoir 87 housed in a cover 86. From the urine suction pump 90, there extends a suction pipe 95 for drawing urine 94 from the urine reservoir 87, and a discharge pipe 96 for discharging the drawn urine. A nozzle 97 extends from the air pump 91 for ejecting air to blow excessive urine off the test paper 92.

To measure constituents of urine, the user attaches the test paper 92 to the holder 93, and then the urine suction pump 90 is actuated to apply urine to the test paper 92 and the air pump 91 is actuated to blow away excessive urine from the test paper 92. Then, the test paper 92 is detached from the holder 93, and inserted into a slot 99 of a sensor 98 which is housed in the cover 86.

In FIG. 11, a rotary holder 119 and a lifter 120 are disposed in a cover 106. The lifter 120 comprises a drum 121 rotatable by a motor, a wire 122 wound around the drum 121, and a cup 123 attached to the lower end of the wire 122. In operation, urine 114 is scooped from a urine reservoir 107 by the cup 123 attached to the wire 122. A piece of test paper 112 is gripped by the rotary holder 119 turned upwardly, and then brought obliquely downwardly as shown. The cup 123 is lifted by the drum 121 until the tip end of the test paper 112 held by the rotary holder 119 is dipped in the urine 114 in the cup 123. The rotary holder 119 is then turned to bring the test paper 112 with the urine applied thereto toward a sensor 118.

It is practically preferable if a toilet with a device for measuring constituents of voided urine is further equipped with a device for measuring body temperature, body weight, blood pressure, and pulse rate, and also with a device for washing body parts, and also if various measured values are recorded in an IC card. Such an arrangement is shown in FIGS. 12 and 13 which illustrate a seventh embodiment and also in FIGS. 14 through 16 which show an eighth embodiment.

Figure 12:
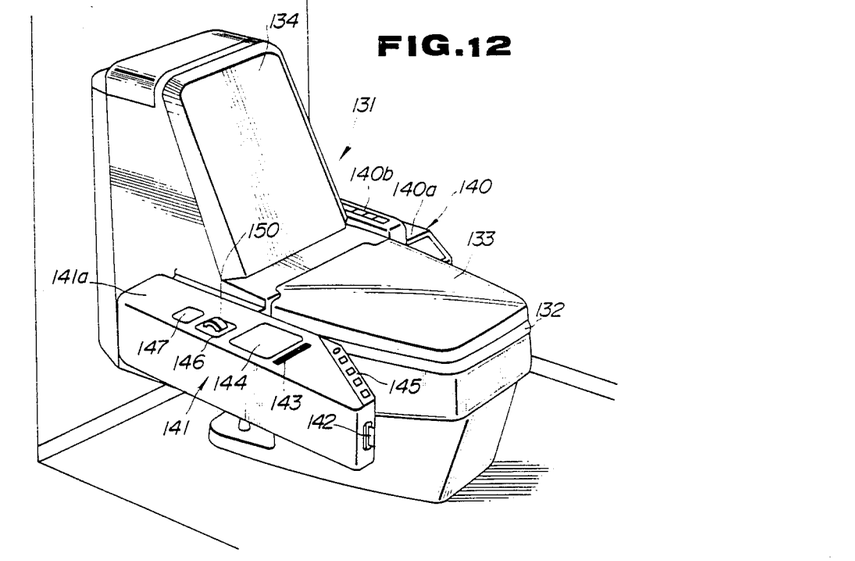
FIG. 12 is a perspective view of a toilet having a device for measuring constituents of voided urine according to a seventh embodiment of the present invention.
Figure 13:
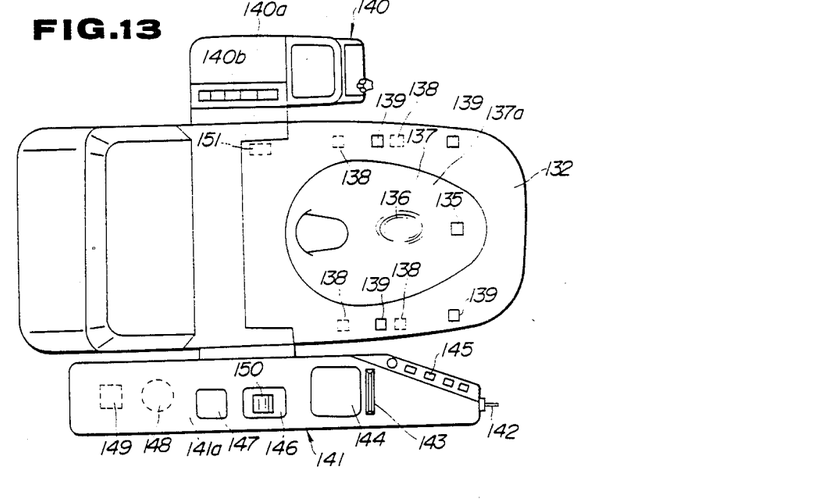
FIG. 13 is a plan view of the toilet shown in FIG. 12.

As shown in FIGS. 12 and 13, a seat 132 and a cover 133 are openably and closably disposed on a front upper surface of a toilet 131, and a box 134 housing a water tank therein is disposed in a rear portion of the toilet 131.

The toilet 131 has a bowl surface 137 including a portion 137a to which voided urine is applied, with a body temperature sensor 135 being embedded in the portion 137a. The bowl surface 137 also includes a urine reservoir 136 which is sightly lower than the body temperature sensor 135. To the seat 132, there are attached body weight sensors 138 for measuring the weight of a user seated on seat 132, and heart rate sensors 139 for contacting the thighs of the user seated on the seat 132 to measure the heart rate or pulse rate of the user.

A control unit 140 for operating a device for washing body parts of the user, including buttons 140b, and a measuring unit assembly 141 are disposed on respective lateral sides of the toilet 131, the control unit 140 and the measuring unit assembly 141 being covered with covers 140a, 141a, respectively. The measuring unit assembly 141 disposed on the righthand side (lower side as shown) of the toilet 131 includes, substantially in order from the front end, an IC card slot 142, a test paper slot 143, a urine constituent sensor 144, a control panel 145 for measuring the urine constituents and blood pressure, a storage box 146 housing a blood pressure sensor 150, a moisture-resistant storage case 147 for storing pieces of test paper, a loud speaker 148, and a temperature/humidity sensor 149.

An IC card is used to record data of an individual user. The blood pressure sensor 150 housed in the storage box 146 is in the form of a ring in which a user's finger can be inserted, and can be pulled upwardly out of the storage box 146 so that the blood pressure of the user can be measured at substantially the same height as the heart of the user. The loud speaker 148 serves to indicate to the user a procedure for examining excreted urine or a procedure for operating the control unit 140 after a seat sensor 151 disposed on a rear portion of the seat 132 has detected that the user is seated on the seat 132. The temperature/humidity sensor 149 serves to check the temperature and humidity at the time the various data of the user are measured.

For measuring various constituent data of urine, a piece of test paper is taken out of the storage case 147, and dipped in a pool of voided urine in the urine reservoir 136. Then, the test paper is lifted and inserted into the test paper slot 143, whereupon the sensor 144 measures glucose, albumin, urobilin, and occult blood of the urine under examination based on degrees of coloration of the test paper.

The measured urine data, and the body weight, the blood pressure, the body temperature, and the pulse rate are recorded in the IC card.

Figure 14:
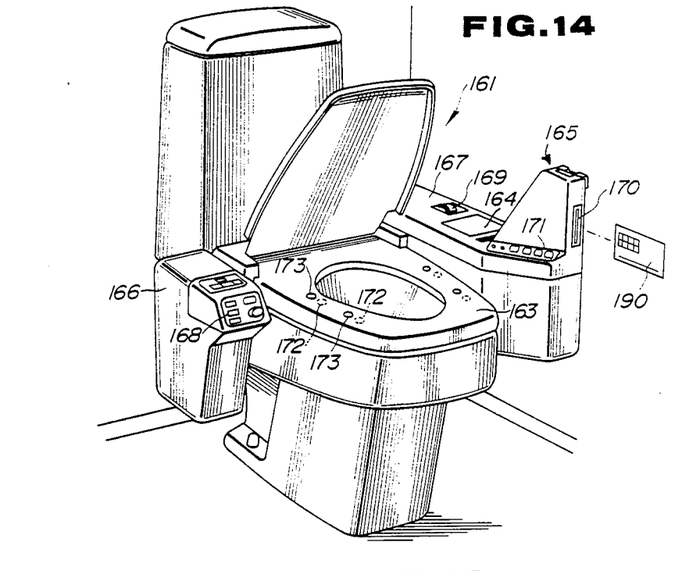
FIG. 14 is a perspective view of a toilet having a device for measuring constituents of voided urine according to an eighth embodiment of the present invention.

In FIG. 14, a control unit housing 166 for operating a device for washing body parts of the user is mounted on the righthand side (lefthand side as shown) of a toilet 161 which has the same urine reservoir as that shown in FIG. 13. The control unit housing 166 has a control panel 168 on its front face. A measuring unit housing 167 mounted on the lefthand side of the toilet 161 houses a blood pressure sensor 169, a urine constituent analyzer 164, and an IC card recorder 165, and has on its front face a slot 170 for inserting an IC card 190 and a control panel 171. The toilet 161 includes a seat 163 incorporating weight sensors 172 and heart rate sensors 173. A body temperature sensor (not shown) is embedded in a bowl surface (not shown) of the toilet 161.

Figure 15:
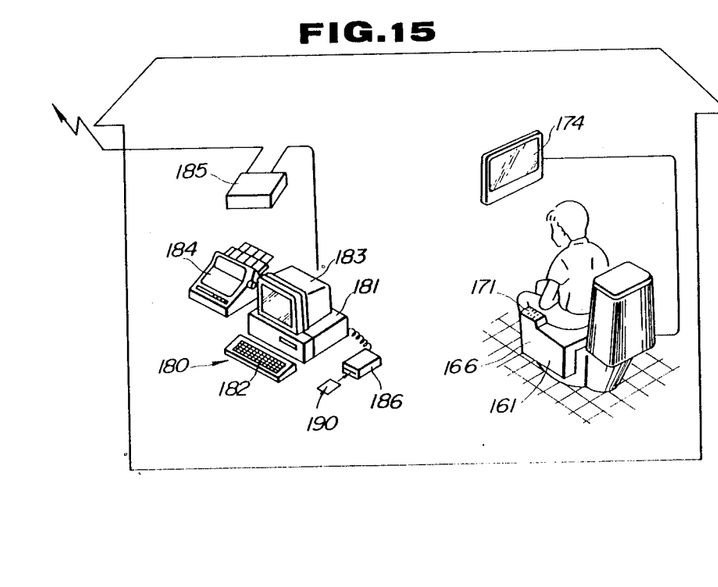
FIG. 15 is a schematic view illustrating the relationship between the toilet of FIG. 14 and a computer for processing measured data from the toilet.

As shown in FIG. 15, a display unit 174 is mounted on a wall of a bathroom in which the toilet 161 is installed. The display unit 174 serves to display data measured by various measuring devices. The display unit 174 is illustrated by way of example in FIG. 16.

A computer system 180 is installed in another room and includes a computer 181 connected to peripherals such as a key board 182, a display unit 183, a printer 184, a modem 185, and a card reader 186.

Figure 16:
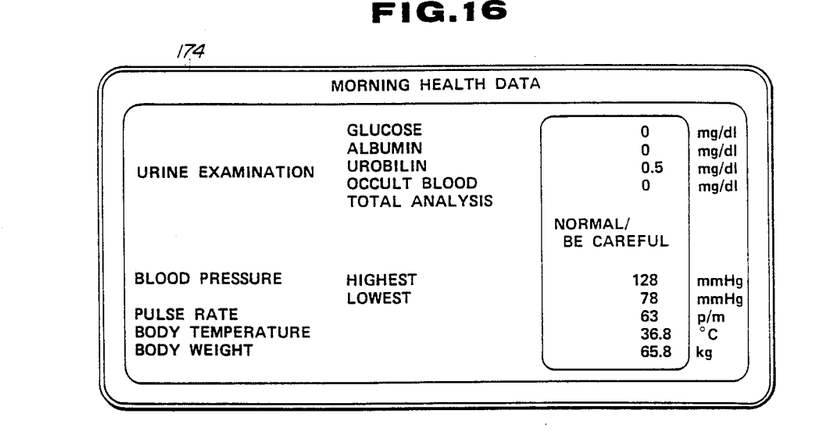
FIG. 16 is an elevational view of a display unit for displaying measured data on a wall.

When the IC card 190 assigned to an individual is inserted into the IC slot 170 of the toilet 161, various health data such as a body temperature, a body weight, a heart or pulse rate, a blood pressure, and various constituents of voided urine such as glucose, albumin, urobilin, and occult blood, which are measured while the user is voiding urine, are displayed on the display unit 174 as shown in FIG. 16. At the same time, these health data are recorded in the IC card 190.

Then, the IC card 190 is inserted into the card reader 186 of the computer system 180 to store the data recorded in the IC card 190 into a memory of the computer and also to cause time-dependent changes in the data, which are statistically given based on the past data, to be displayed on the display unit 183 or printed out. Moreover, the data recorded in the IC card 190 are transmitted to central medical care facilities such as a hospital through the modem 185 which contains a modulator for transmitting digital signals with a carrier over a transmission line.

With the embodiments shown in FIGS. 12 through 16, data measured by various measuring devices are recorded in the IC card, and the card reader for reading the recorded data from the IC card is associated with the computer which is separate from the toilet. Therefore, data management can easily be performed. For example, the daily health data of a user thus obtained can be presented to a doctor simply by bringing the IC data to a hospital.

Although there have been described what are at present considered to be the preferred embodiments of the present invention, it will be understood that the invention may be embodied in other specific forms without departing from the spirit or essential characteristics thereof. The present embodiments are therefore to be considered in all aspects as illustrative, and not restrictive. The scope of the invention is indicated by the appended claims rather than by the foregoing description.

We claim:

1. A toilet comprising:
   a bowl surface including a urine receiving surface;
   a urine reservoir having a surface contiguous to said bowl surface and said urine receiving surface; and
   a measuring device for measuring constituents of urine sampled from said urine reservoir, wherein said measuring device comprises measuring means for measuring said constituents of urine from a test sample on a piece of test paper, said measuring means supported by said toilet and having a slot adapted for receiving therein a piece of test paper including said test sample, said measuring means further including a urine sensor means for sensing said constituents of urine contained in said test sample included in said test paper.

2. A toilet according to claim 1, further comprising a laterally outwardly projecting portion, said urine reservoir being disposed in said laterally outwardly projecting portion.

3. A toilet according to claim 1, wherein said urine reservoir is formed on said bowl surface.

4. A toilet according to claim 1, further comprising:
   sensing means for detecting completion of measurement of the constituents of urine; and
   washing means for flushing said bowl surface and the surface of said urine reservoir with water in response to detection of the completion of measurement of the constituents of urine.

5. A toilet according to claim 4, further comprising a seat, said sensing means comprising a seat sensor disposed on said seat for detecting when a user is seated on said seat.

6. A toilet according to claim 1, further comprising air blowing means disposed near said urine reservoir for blowing air to a piece of test paper impregnated with the sampled urine.

7. A toilet according to claim 6, wherein said air blowing means comprises an air pump attached to a portion of the toilet and an air discharge pipe extending from said air pump toward a position above said urine reservoir.

8. A toilet according to claim 1, further comprising:
   washing means for flushing said bowl surface and the surface of said urine reservoir with water; and
   discharge means for discharging flushing water from said urine reservoir.

9. A toilet according to claim 8, wherein said discharge means comprises an air pump attached to a portion of the toilet and an air discharge pipe extending from said air pump toward a position near said urine reservoir.

10. A toilet according to claim 1, further comprising lifting/lowering means disposed above said urine reservoir for lowering and lifting a piece of test paper toward and away from said urine reservoir.

11. A toilet according to claim 10, wherein said lifting/lowering means comprises a drum rotatable by a motor, an elongate member wound around said drum, and a clip attached to a tip end of said elongate member for holding the piece of test paper.

12. A toilet according to claim 11, wherein said device includes means for measuring constituents of urine applied to the piece of test paper held by said clip.

13. A toilet according to claim 10, further comprising a cover disposed above said urine reservoir in covering relation to a space above the urine reservoir, said lifting/lowering means and said device being disposed in said cover.

14. A toilet according to claim 10, wherein said lifting/lowering means comprises a drum rotatable by a motor and a piece of test paper wound around said drum.

15. A toilet according to claim 14, wherein said device includes means for measuring constituents of urine applied to a lower end of the piece of test paper depending from said drum, said toilet further comprising cutting means disposed more closely to said drum than said device along said piece of test paper for cutting off the piece of test paper.

16. A toilet according to claim 1, further comprising:
    holder means disposed above said urine reservoir for holding a piece of test paper; and
    applicator means for applying urine from said urine reservoir to the piece of test paper held by said holder means.

17. A toilet according to claim 16, wherein said applicator means comprises a drum rotatable by a motor, an elongate member wound around said drum, and a cup attached to said elongate member.

18. A toilet according to claim 16, wherein said applicator means comprises a suction pump, a suction pipe extending from said suction pump to said urine reservoir, and a discharge pipe extending from said suction pipe to the piece of test paper held by said holder means.

19. A toilet according to claim 16, further comprising a cover disposed above said urine reservoir in covering relation to a space above the urine reservoir, said holder means and said device being disposed in said cover.

20. A toilet according to claim 1, further comprising a storage case mounted on one side of the toilet for storing a piece of test paper therein, said device being mounted on said one side, and a single cover covering said storage case and said device.

21. A toilet according to claim 1, further comprising a recorder connected to said device for recording data of measured constituents in an IC card.

22. A toilet according to claim 1, further comprising a card reader for reading out the data recorded in said IC card, and a computer connected to said card reader for processing the data read by said card reader.

23. A toilet according to claim 1, wherein said measuring means is supported by said toilet on one lateral side thereof.

24. A toilet comprising:
    a bowl surface including a urine receiving surface;
    a urine reservoir having a shallow concave surface contiguous to said bowl surface and said urine receiving surface for pooling therein a portion of urine received at said urine receiving surface, said concave surface being gradually inclined for allowing said urine to flow by gravity from said urine receiving surface to said urine reservoir; and
    a measuring device for measuring constituents of urine sampled from said urine reservoir, wherein said device for measuring comprises measuring means supported by said toilet and having a slot adapted for receiving therein a piece of test paper containing a urine sample, said measuring means further including a urine sensor provided for sensing said constituents of urine in said urine sample contained in said test paper.

25. A toilet according to claim 24, wherein said measuring means is supported by said toilet on one lateral side thereof.

* * * * *